United States Patent
Cooper

(10) Patent No.: US 7,267,656 B2
(45) Date of Patent: Sep. 11, 2007

(54) ANKLE BRACE

(75) Inventor: Ronald Cooper, Olathe, KS (US)

(73) Assignee: Cooper Medical Company, Inc., Olathe, KS (US)

( * ) Notice: Subject to any disclaimer, the term of this patent is extended or adjusted under 35 U.S.C. 154(b) by 153 days.

(21) Appl. No.: 11/335,083

(22) Filed: Jan. 19, 2006

(65) Prior Publication Data

US 2007/0167896 A1      Jul. 19, 2007

(51) Int. Cl.
*A61F 5/00* (2006.01)
(52) U.S. Cl. .......................................... 602/27; 602/28
(58) Field of Classification Search ............ 602/27–28; 606/27–28
See application file for complete search history.

(56) References Cited

U.S. PATENT DOCUMENTS

| | | | | |
|---|---|---|---|---|
| 2,994,322 A | * | 8/1961 | Cullen et al. | 602/27 |
| 4,753,229 A | * | 6/1988 | Sutherland | 602/27 |
| 4,962,768 A | * | 10/1990 | Stromgren et al. | 602/27 |
| 5,050,620 A | | 9/1991 | Cooper | |
| 5,067,486 A | * | 11/1991 | Hely | 602/27 |
| 5,676,641 A | * | 10/1997 | Arensdorf et al. | 602/27 |
| 5,944,678 A | * | 8/1999 | Hubbard | 602/27 |

\* cited by examiner

*Primary Examiner*—Michael Peffley
(74) *Attorney, Agent, or Firm*—Hovey Williams LLP

(57) ABSTRACT

An ankle brace comprising a pliable underliner and including medial and lateral straps including forward and rear strap segments which allow a wearer to independently adjust the tension provided to the forefoot and heel. The ankle brace is capable of being worn on either foot and with conventional footwear and inhibits inversion and/or eversion of the wearer's foot.

18 Claims, 3 Drawing Sheets

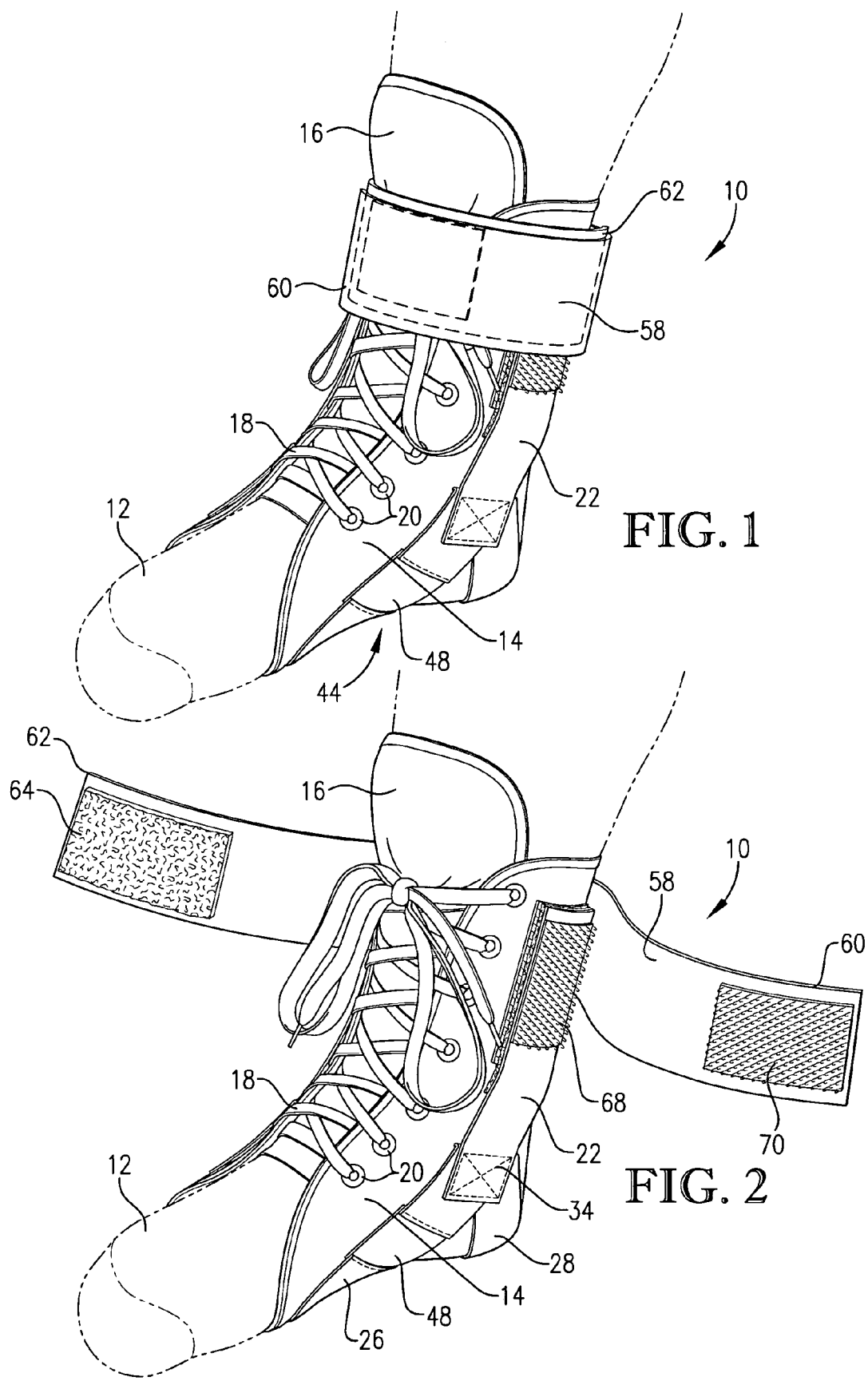

ANKLE BRACE

BACKGROUND OF THE INVENTION

1. Field of the Invention

The present invention generally pertains to an ankle brace which enables the wearer to participate in regular home, work and athletic activities while protecting an injured ankle or an ankle vulnerable to injury. More specifically, the ankle brace allows the wearer to provide desired levels of forefoot and heel control through a single strap.

2. Description of the Prior Art

During the course of routine activities, particularly athletic events, the human ankle is subjected to various shocks and strains which may lead to injury such as a sprain. To allow continued activity of a person having an injured ankle or as a prophylactic measure against injury, adhesive tape has been used to wrap an ankle. The use of adhesive tape presents a number of drawbacks. Considerable time can be spent in taping an ankle, and the tape must be discarded after each use. In addition, the tape is often inflexible and results in discomfort and loss of motion during wear.

Reusable braces have been developed which eliminate some of the disadvantages of adhesive tape. However, due to the constraint that those braces must be designed for enabling the wearer to wear his or her existing shoes and thus be closely conforming to the foot, such reusable braces may not provide a sufficient degree of foot or ankle control to adequately protect the ankle from injury. Also, certain ankle braces are designed for either the right or left foot and cannot be worn on both the right and left feet.

Therefore, a need exists in the art for an ankle brace that enables the wearer to control both forefoot and heel support in a simple and easily adjustable manner. The ankle brace should also permit a sufficient range of motion for the ankle so as to allow the wearer to engage in regular or athletic activities and be capable of use on both the left and right feet.

SUMMARY OF THE INVENTION

The present invention overcomes the above problems by an ankle support system that provides the wearer with the ability to control forefoot tension and calcaneal tension through pull straps located on the lateral and medial sides of the brace.

According to one embodiment of the present invention, an ankle brace for protecting a human ankle is provided comprising: an underliner comprising a pliable material for receiving and fitting over a wearer's foot and presenting a sole portion at the bottom thereof; a medial strap that is releasably attachable to the underliner, the medial strap including diverging forward and rear medial strap segments extending from the medial strap and secured to the sole portion; and a lateral strap that is releasably attachable to the underliner, the lateral strap including diverging forward and rear lateral strap segments extending from the lateral strap and secured to the sole portion.

In another embodiment according to the present invention, an ankle brace for protecting a human ankle is provided comprising: an underliner comprising a pliable material for receiving and fitting over a wearer's foot and presenting a sole portion at the bottom thereof; a medial strap presenting a remote end that is releasably attachable to the underliner, the medial strap including diverging forward and rear medial strap segments extending from the medial strap and secured to the sole portion; a lateral strap presenting a remote end that is releasably attachable to the underliner, the medial strap including diverging forward and rear lateral strap segments extending from the lateral strap and secured to the sole portion; a medial fastener located on the underliner relatively proximate the medial side of the ankle for releasably receiving the medial strap remote end and holding the lateral strap in tension; a lateral fastener located on the underliner relatively proximate the lateral side of the ankle for releasably receiving the lateral strap remote end and holding the lateral strap in tension; and an ankle strap secured to and circumferentially extending around the underliner proximate the lower leg of the wearer in covering relationship to the remote end of the medial strap and the remote end of the lateral strap.

In yet another embodiment according to the present invention, a method of protecting a human ankle is provided comprising the steps of: placing an underliner comprising a pliable material over a wearer's foot, the underliner including—a medial strap that is releasably attachable to the underliner, the medial strap including diverging forward and rear medial strap segments extending from the medial strap and secured to the sole portion; a lateral strap that is releasably attachable to the underliner, the medial strap including diverging forward and rear lateral strap segments extending from the lateral strap and secured to the sole portion; and an ankle strap secured to the underliner proximate the wearer's lower leg; securing the medial strap under tension to a fastener located relatively proximate the medial side of the ankle; securing the lateral strap under tension to a fastener located relatively proximate the lateral side of the ankle; and fastening the ankle strap around a portion of the wearer's lower leg and in covering relationship to at least a portion of the medial and lateral straps.

BRIEF DESCRIPTION OF THE DRAWINGS

FIG. 1 is a front perspective view of an ankle brace according to the present invention that is fully secured to the foot of a wearer;

FIG. 2 is a perspective view of the ankle brace with the ankle strap unfastened;

DETAILED DESCRIPTION OF THE PREFERRED EMBODIMENT

Figure 3:
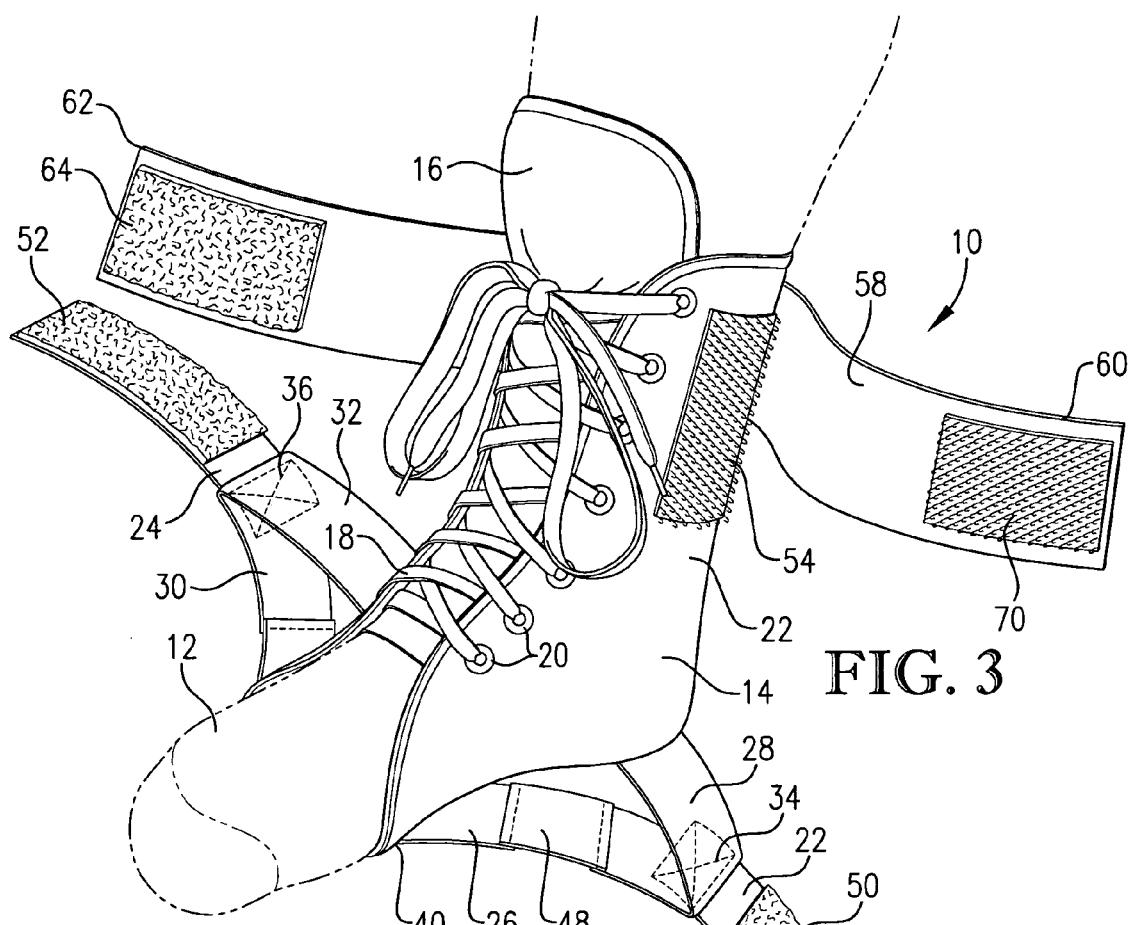
FIG. 3 is a perspective view of the ankle brace with both the lateral and medial straps unfastened from the underliner.

The following description pertains to preferred ankle braces according to the present invention. It is to be understood, however, that these embodiments are provided by way of illustration and nothing therein should be taken as a limitation upon the overall scope of the invention.

Turning now to FIGS. 1-4, an ankle brace 10 is shown worn about a human foot 12 and ankle. Brace 10 comprises an underliner 14 that includes a tongue 16 and a lace 18. Underliner 14 is preferably formed from a pliable material, with woven textile materials (made from natural or synthetic fibers) being preferred. In preferred embodiments, the pliable material is relatively inelastic so as not to stretch appreciably when worn about foot 12. Also, it is preferable for underliner 14 to be of unitary construction, with the exception of tongue 16 which may be stitched to the underliner.

A plurality of eyelets 20 are formed in underliner 14 through which lace 18 is threaded. Lace 18 is loosened in order to facilitate insertion of foot 12 into brace 10 and may subsequently be drawn taut to firmly secure brace 10 about foot 12 and ankle.

Brace 10 further comprises a medial strap 22 and a lateral strap 24. Medial strap 22 comprises a forward strap segment 26 and a rear strap segment 28. Likewise, lateral strap 24 also comprises a forward and a rear strap segment 30, 32, respectively. As shown in FIG. 3, strap segments 26, 28 are joined to medial strap 22 at a common point of attachment 34. Preferably, this attachment is made by stitching strap segments 26, 28 to strap 22. In the same way, strap segments 30, 32 are joined to lateral strap 24 at a common point of attachment 36.

Figure 5:
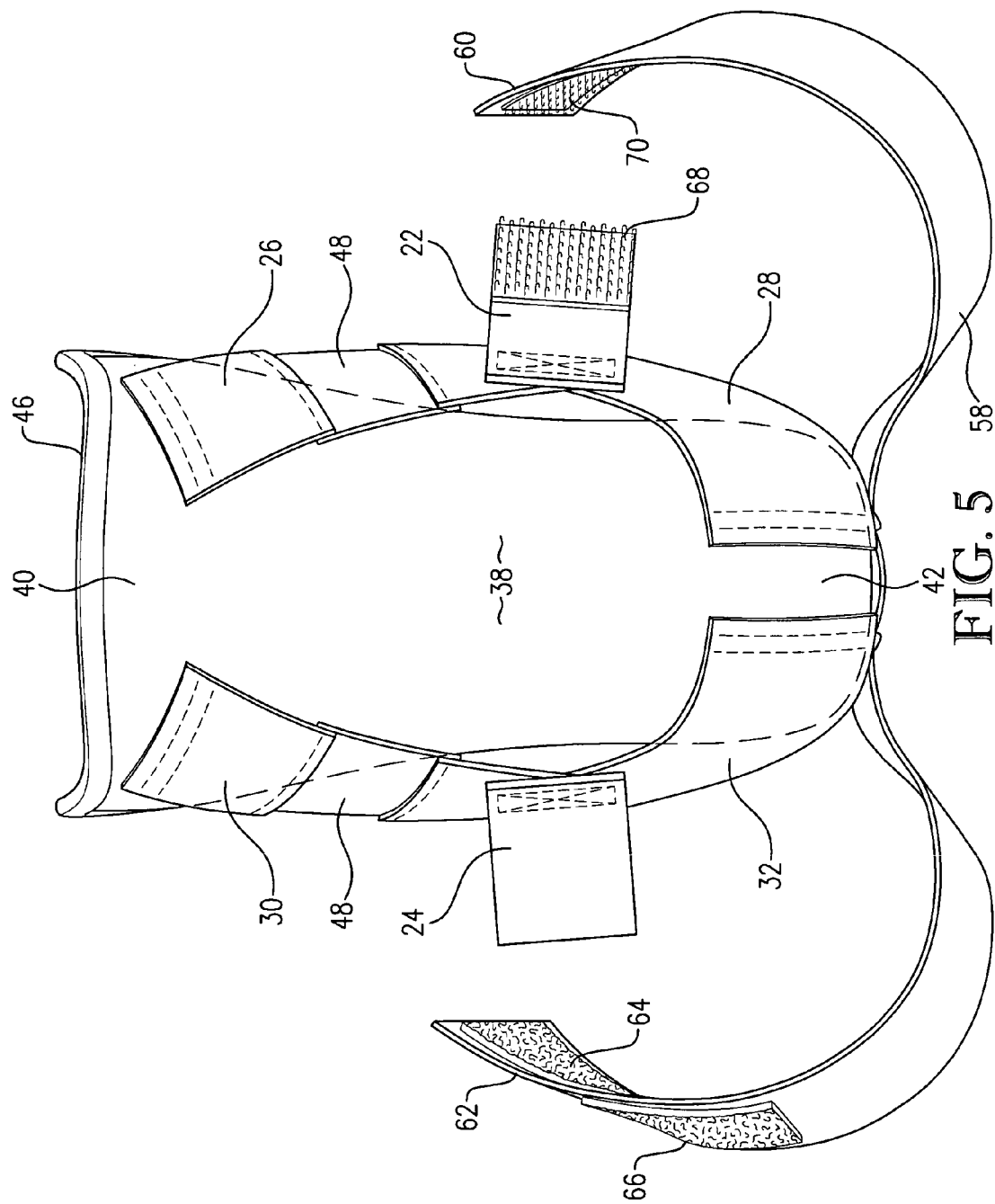
FIG. 5 is a bottom perspective view showing the points of attachment of the forward and rear strap segments to the underliner sole.

Turning to FIG. 5, strap segments 26-32 are fixedly secured to a sole portion 38 of underliner 14. Sole portion 38 includes a forefoot section 40 and a heel section 42. Forefoot section 40 is generally located forward of an arch 44 of the wearer's foot, whereas heel section 42 is generally located aft of arch 44. Forefoot section 40 presents a forward edge 46, which when underliner 14 is worn over foot 12, is located adjacent to, and preferably in covering relationship to, the metatarsal phalangeal joints of the wearer's foot. Heel section 42 is preferably in covering relationship to at least a portion of, and more preferably substantially all of, the wearer's heel.

In preferred embodiments, strap segments 26-32 are stitched to sole portion 38, and more preferably stitched only to sole portion 38. Strap segments 26-32 are generally not attached to any other area of underliner 14. In this manner, segments 26-32 can be used to apply forces to sole portion 38 in order to inhibit inversion (outside of the foot turning toward the arch) and eversion (outside of the foot pivoting upward toward the outer side of the ankle) of foot 12. Also, it is preferable for adjacent medial and lateral strap segments (i.e., segments 26 and 30 and segments 28 and 32) to not overlap each other, be formed from a unitary piece of material, or be directly attached to each other. This enables the tension in each of strap segments 26-32 to be independently adjustable in order to apply differing levels of force to the medial and lateral sides of sole portion 38 as desired.

Strap segments 26, 30 each may be formed from a continuous piece of pliable, yet relatively inelastic material. However, as shown in the figures, segments 26, 30 may comprise an intermediate section of material 48 which allows for additional forefoot plantar flexion, which generally accompanies running activities. Intermediate section 48 may be formed from a resilient, yet stretchable, material including, but not limited to, neoprene, elastic fabrics, and natural rubbers. However, section 48 need not be stretchable and can be formed from the same, relatively inelastic material as strap segments 26, 30.

Straps 22, 24 further comprise a medial fastening element 50 and a lateral fastening element 52 located proximate the remote ends of each strap. Fastening elements 50, 52 are capable of mating with corresponding underliner medial fastener 54 and lateral fastener 56 in order to secure straps 22, 24 to underliner 14. In the embodiment depicted in the figures, fastening elements 50, 52 and fasteners 54, 56 comprise hook and pile material, such as that sold under the trademark VELCRO. However, it is within the scope of the present invention for other types of fasteners such as snaps or buttons to be used. Fastening elements and fasteners 50-56 are capable of holding straps 22, 24 in tension thereof. In this manner, forces are applied through straps 22, 24 and strap segments 26-32 upon forefoot and heel sections 40, 42 of the underliner sole portion.

Figure 4:
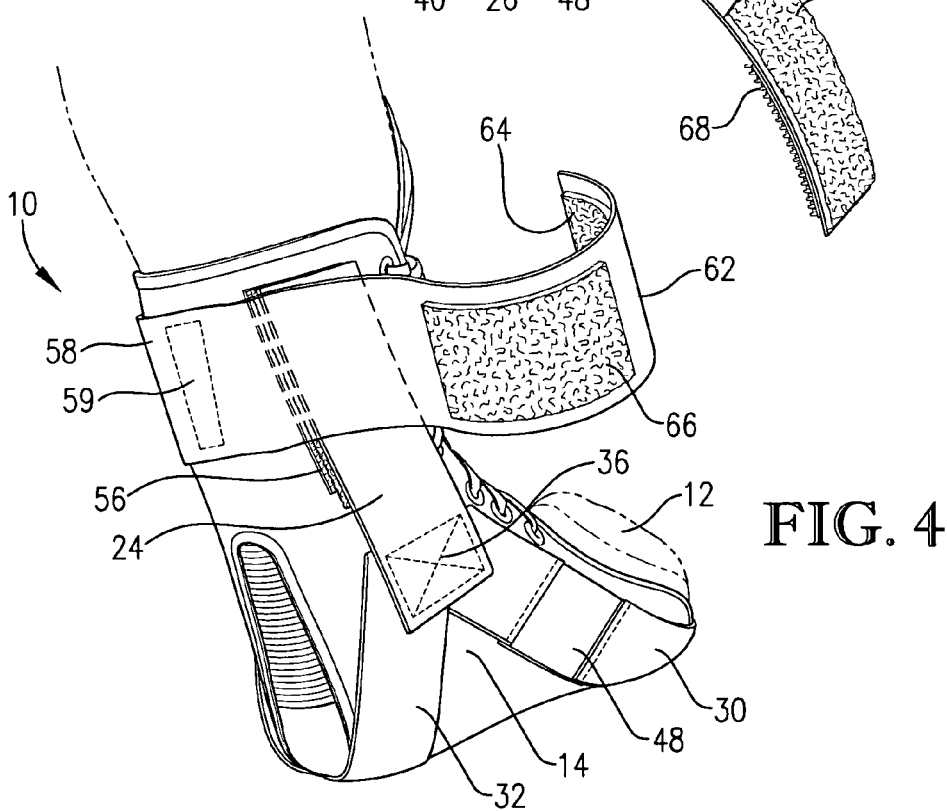
FIG. 4 is a rear perspective view of the ankle brace with the ankle strap unfastened.

Ankle brace 10 further includes an ankle strap 58 which is secured to underliner 14. Ankle strap 58, as shown in FIG. 4, is stitched to underliner 14 at attachment point 59 below the wearer's calf and presents a medial end 60 and a lateral end 62. Ankle strap 58, when fully secured, circumferentially extends around underliner 14 proximate the lower leg of the wearer and at least partially covers a portion of medial and lateral straps 22, 24. Lateral end 62 includes an inner fastening element 64 and an outer fastening element 66 attached thereto. As shown in the Figures, elements 64, 66 comprise a hook or pile material, however, any appropriate type of fastener may be used which is capable of holding ankle strap 58 in tension. Inner fastening element 64 is configured for attachment with a medial strap outer fastening element 68, also formed from a hook or pile material. Ankle strap medial end 60 includes a fastening element 70 which is configured for attachment to outer fastening element 66. Again, fastening element 70 is formed from a hook or pile material.

A person desiring to wear ankle brace 10 first slides his or her foot 12 into underliner 14 and tightens lace 18. Next, the wearer, with ankle strap 58 unfastened, secures the remote ends of medial and lateral straps 22, 24 to underliner 14 via fasteners 50-56. In securing medial and lateral straps 22, 24, the wearer pulls on the straps thereby creating tension in strap segments 26-32 which in turn apply a force to the wearer's forefoot or heel. Thus, forefoot and heel control is achieved by the wearer pulling upon a single medial strap 22 and a single lateral strap 24. In this manner, ankle brace 10 inhibits undesired inversion or eversion of the foot.

Once medial and lateral straps 22, 24 are secured lateral end 62 of ankle strap 58 is drawn across the front of ankle brace 10 and inner fastening element 64 is attached to medial strap outer fastening element 68. Preferably, fastening elements 64, 68 hold the lateral end portion 62 of strap 58 in tension. Next, medial end 60 is pulled across the front of ankle brace 10 substantially on top of lateral end 62 and fastening element 70 secured to outer fastening element 66. Fastening elements 66, 70 preferably hold the medial end portion 60 of strap 58 in tension. Thus, ankle strap 58 serves two functions: to provide additional support to the wearer's ankle and to protect the remote ends of medial and lateral straps 22, 24 from loosening or becoming inadvertently detached from underliner 14 during physical activities.

Ankle brace 10 is adjustable for a range of foot sizes and is configured to be worn on either the left or right foot. Preferably, the brace is universal meaning that the same brace could be worn on a wearer's left foot and on the wearer's right foot. Strap segments 26-32 through medial and lateral straps 22, 24 allow for control of both inversion and eversion sprain mechanisms. Brace 10 presents a relatively thin profile and construction thereby making it suitable for use with existing footwear (i.e., brace 10 may be worn underneath a shoe). Brace 10 may be worn to reduce the risk of incurring additional injury to a wearer with acute or chronic ankle problems and also to prevent injury to a healthy ankle.

I claim:

1. An ankle brace for protecting a human ankle comprising:
   an underliner comprising a pliable material for receiving and fitting over a wearer's foot and presenting a sole portion at the bottom thereof;
   a medial strap presenting a medial strap remote end that is releasably attachable to said underliner, said medial strap including diverging forward and rear medial strap segments extending from said medial strap and secured to said sole portion; and a lateral strap presenting a lateral strap remote end that is releasably attachable to said underliner, said lateral strap including diverging forward and rear lateral strap segments extending from said lateral strap and secured to said sole portion.

2. The ankle brace of claim 1, said brace further comprising an ankle strap secured to and configured to circumferentially extend around said underliner proximate the lower leg of the wearer in covering relationship to said at least a portion of said medial and lateral straps.

3. The ankle brace of claim 1, said forward medial and lateral strap segments each comprising an intermediate section of material stitched therein.

4. The ankle brace of claim 1, said sole portion presenting forefoot and heel sections, said forward medial and lateral strap segments being secured to said forefoot section, and said rear medial and lateral strap segments being secured to said heel section.

5. The ankle brace of claim 4, said forward medial and lateral strap segments configured to be secured to the sole portion of said underliner at a location forward of an arch of the wearer's foot, and said rear medial and lateral strap segments configured to be secured to the sole portion of said underliner at a location aft of an arch of the wearer's foot and proximate the wearer's heel.

6. The ankle brace of claim 5, said brace further comprising a medial fastener and a lateral fastener for releasably receiving said medial and lateral straps, respectively, in tension.

7. The ankle brace of claim 6, said forward and rear strap segments applying a force to the underliner proximate the forefoot and heel sections thereof for inhibiting inversion and eversion of the wearer's foot.

8. An ankle brace for protecting a human ankle comprising:

an underliner comprising a pliable material for receiving and fitting over a wearer's foot and presenting a sole portion at the bottom thereof;

a medial strap presenting a remote end that is releasably attachable to said underliner, said medial strap including diverging forward and rear medial strap segments extending from said medial strap and secured to said sole portion;

a lateral strap presenting a remote end that is releasably attachable to said underliner, said medial strap including diverging forward and rear lateral strap segments extending from said lateral strap and secured to said sole portion;

a medial fastener located on said underliner relatively proximate the medial side of the ankle for releasably receiving said medial strap remote end and holding said lateral strap in tension;

a lateral fastener located on said underliner relatively proximate the lateral side of the ankle for releasably receiving said lateral strap remote end and holding said lateral strap in tension; and an ankle strap secured to and configured to circumferentially extend around said underliner proximate the lower leg of the wearer in covering relationship to said remote end of said medial strap and said remote end of said lateral strap.

9. The ankle brace of claim 8, said forward medial and lateral strap segments each comprising an intermediate section of material stitched therein.

10. The ankle brace of claim 8, said sole portion presenting forefoot and heel sections, said forward medial and lateral strap segments being secured to said forefoot section, and said rear medial and lateral strap segments being secured to said heel section.

11. The ankle brace of claim 10 said forward and rear strap segments applying a force to the forefoot and heel sections of said underliner for inhibiting inversion and eversion of the wearer's foot.

12. The ankle brace of claim 8, said medial and lateral fasteners comprising a hook or pile material.

13. The ankle brace of claim 12, said medial and lateral strap remote ends including sections of hook or pile material capable of attachment to said medial and lateral fasteners.

14. A method of protecting a human ankle comprising the steps of:

placing an underliner comprising a pliable material over a wearer's foot, said underliner including a medial strap that is releasably attachable to said underliner, said medial strap including diverging forward and rear medial strap segments extending from said medial strap and secured to said sole portion;

a lateral strap that is releasably attachable to said underliner, said lateral strap including diverging forward and rear lateral strap segments extending from said lateral strap and secured to said sole portion; and an ankle strap secured to said underliner proximate the wearer's lower leg;

securing said medial strap under tension to a fastener located relatively proximate the medial side of the ankle;

securing said lateral strap under tension to a fastener located relatively proximate the lateral side of the ankle; and fastening said ankle strap around a portion of the wearer's lower leg and in covering relationship to at least a portion of said medial and lateral straps.

15. The method of claim 14, said sole portion presenting forefoot and heel sections, said forward medial and lateral strap segments being secured to said forefoot section, and said rear medial and lateral strap segments being secured to said heel section.

16. The method of claim 15, including the step of tensioning said forward and rear strap segments so as to apply force to said forefoot and heel sections so as to inhibit inversion and eversion of the wearer's foot.

17. The method of claim 14, said fasteners comprising hook or pile material.

18. The method of claim 14, said underliner extending from the base of the wearer's calf to the metatarsal heads of the wearer's foot.

* * * * *